United States Patent [19]

Shimada et al.

[11] Patent Number: 5,192,662
[45] Date of Patent: Mar. 9, 1993

[54] ANTI-GANGLIOSIDE $GD_1A$ MONOCLONAL ANTIBODY MZ, MZ-PRODUCING CELLS AND MZ-CONTAINING REAGENT

[75] Inventors: Shizuo Shimada; Daiji Iwata, both of Mobara; Wakao Sato, Chiba, all of Japan

[73] Assignee: Mitsui Toatsu Chemicals, Inc., Tokyo, Japan

[21] Appl. No.: 241,291

[22] Filed: Sep. 7, 1988

[30] Foreign Application Priority Data

Sep. 7, 1987 [JP] Japan ................... 62-221862

[51] Int. Cl.$^5$ ................ G01N 33/574; G01N 33/532; C07K 15/28
[52] U.S. Cl. .................. 435/7.23; 435/7.2; 435/7.21; 435/172.2; 435/240.27; 436/813; 436/64; 436/548; 530/388.8; 530/388.85
[58] Field of Search ............... 435/172.2, 240.27, 7.2, 435/7.21, 7.23; 436/548, 813, 64; 530/387, 388.8, 388.85; 935/103, 110

[56] References Cited

PUBLICATIONS

J. Cell Biol. Suppl., vol. 0, No. 11, Part D, No. R312, p. 161 (1987).
Endo et al. J. Immunol. 132(4):1324, 1984.
Håkansson et al. J. Biochem. 98:843, 1985.
Hakomori et al. JNCI 71(27:231, 1983.
Köhler et al. Nature 256:495, 1975.

Primary Examiner—Esther L. Kepplinger
Assistant Examiner—Toni R. Scheiner
Attorney, Agent, or Firm—Millen, White, Zelano and Branigan

[57] ABSTRACT

Disclosed is a novel anti-ganglioside $GD_{1a}$ monoclonal antibody (MZ) which is capable of recognizing ganglioside $GD_{1a}$ but is practically incapable of recognizing GalCer, LacCer, $Gb_3$, $Gb_4$, $GA_1$, $GA_2$, $GM_2$, $GM_3$, $GD_{1b}$, $GT_{1b}$, $GQ_{1b}$, Fuc-$GM_1$, $nLc_4$ and sialosyl $nLc_4$; MZ-producing cells; an MZ-containing reagent; and a method for the detection or quantification of $GD_{1a}$ using the reagent, e.g., to diagnose cancer, systematic lupus erythematosus and diseases resulting from organic injury of the nervous system.

10 Claims, 1 Drawing Sheet

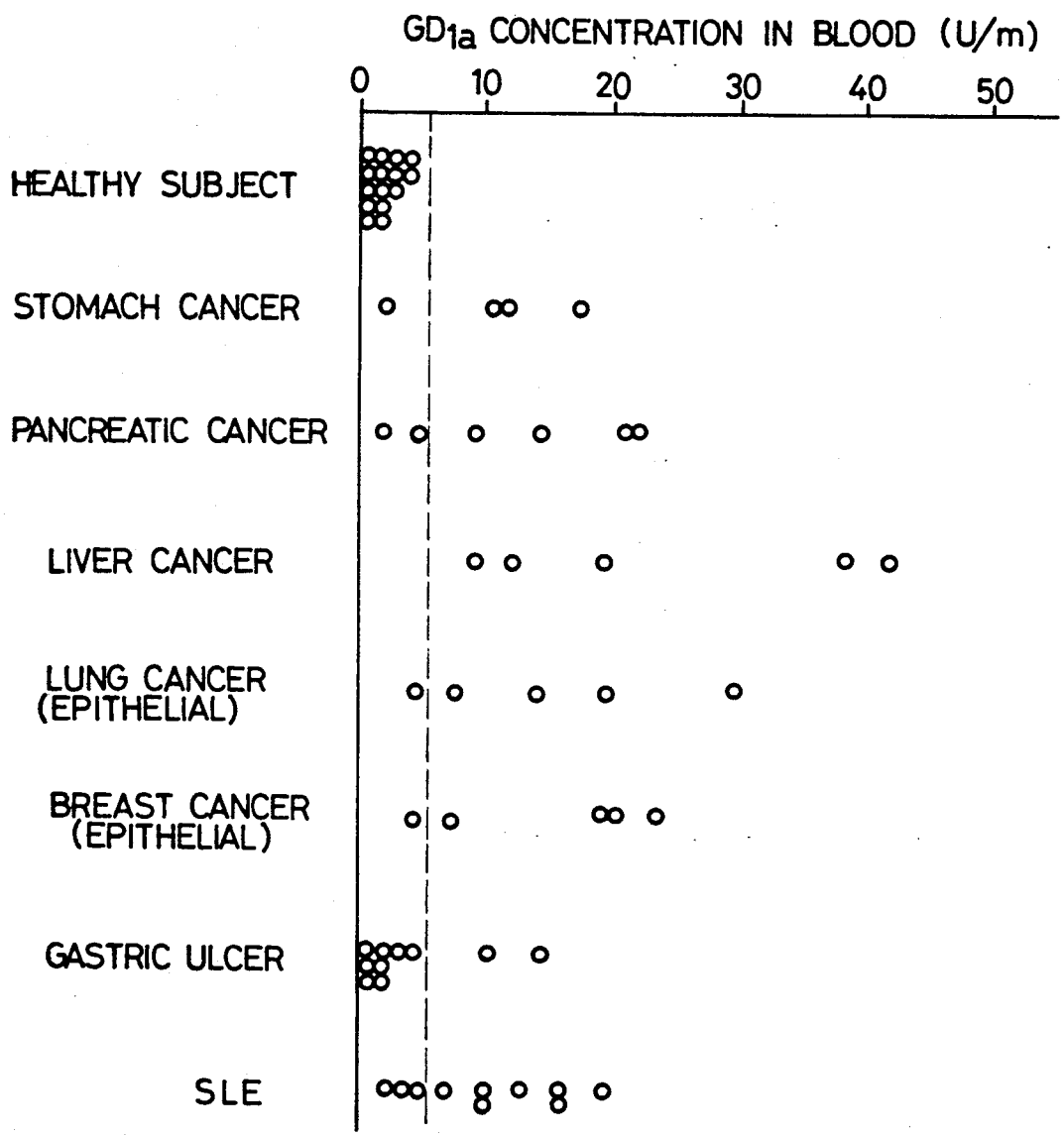

ANTI-GANGLIOSIDE GD₁A MONOCLONAL ANTIBODY MZ, MZ-PRODUCING CELLS AND MZ-CONTAINING REAGENT

BACKGROUND OF THE INVENTION

1. Field of the Invention

This invention relates to a monoclonal antibody against ganglioside $GD_{1a}$, cells capable of producing the antibody, and a reagent containing the antibody and being suitable for use in the detection or quantification of ganglioside $GD_{1a}$.

2. Description of the Related Art

Although various monoclonal antibodies against gangliosides have been proposed, no monoclonal antibody against GDIa has heretofore been known.

Glycolipids are biosubstances which have attracted attention, especially in the investigation of the development, differentiation and canceration of cells. Among such glycolipids, glycosphingolipids containing sialic acid are collectively called "gangliosides". $GD_{1a}$ (hereinafter called merely "$GD_{1a}$") is one of these gangliosides.

$GD_{1a}$ is a substance abundant in human and various animals, especially in the nervous system tissues. The composition of gangliosides in the blood of a cancer patient or a patient with systematic lupus erythematosus (SLE), an autoimmune disease, has been reported to be different significantly from that of healthy people [Journal of Biochemistry, 98, 843 (1985)]. Namely, gangliosides which are contained in the form of immune complexes in the blood are principally composed of $GM_3$ in the case of healthy people, while $GM_3$ is practically unobserved in cancer or SLE patients. Instead, $GM_1$ and $GD_{1a}$ are contained as the principal gangliosides. It is hence possible to estimate whether an individual is suffering from a cancer or SLE, provided the $GD_{1a}$ in his blood can be quantified precisely.

Like $GM_1$ and the like, $GD_{1a}$ is also a principal ganglioside of the nervous system. When one or more diseases are developed due to an organic injury of the nervous system, such as demyelination, $GD_{1a}$ is hence believed to move into the blood or cerebrospinal fluid. Accordingly, it is also possible to estimate from the measurement of the concentration of $GD_{1a}$ in the blood or cerebrospinal fluid whether one is suffering from a disease of the nervous system due to an organic injury.

As methods for the quantification, identification or purification of $GD_{1a}$, immunological methods making use of an antibody specific to $GD_{1a}$ have been found to be useful, in addition to conventional chemical and biochemical methods. As antibodies against $GD_{1a}$, those derived from an antiserum, which are obtained by immunizing a rabbit with $GD_{1a}$ together with a suitable carrier and an immunoadjuvant, have conventionally been used. They are so-called polyclonal antibodies, so that their specificity is not always uniform among production lots or depending upon individual animals employed for the immunization. It has hence been desired to obtain a monoclonal antibody which is free of such drawbacks.

SUMMARY OF THE INVENTION

An object of this invention is to provide a monoclonal antibody against $GD_{1a}$.

Another object of this invention is to provide cells which can produce the monoclonal antibody.

A further object of this invention is to provide a reagent which contains the antibody and is reactive to $GD_{1a}$.

As a result of an extensive investigation, the present inventors have succeeded in producing an anti-$GD_{1a}$ monoclonal antibody which is extremely specific to $GD_{1a}$ and has a high antibody titer unavailable by any conventional technique, leading to completion of this invention.

In a composition aspect of this invention, there is thus provided an anti-ganglioside $GD_{1a}$ monoclonal antibody MZ, hereinafter called simply "MZ", which antibody is capable of recognizing $GD_{1a}$ but practically incapable of recognizing GalCer, LacCer, $Gb_3$, $Gb_4$, $GA_1$, $GA_2$, $GM_1$, $GM_2$, $GM_3$, $GD_{1b}$, $GT_{1b}$, $GQ_{1b}$, Fuc-$GM_1$, $nLc_4$ and sialosyl $nLc_4$.

In another composition aspect of this invention, there is also provided a hybridoma HbMZ formed by fusing antibody-producing cells derived from a $GD_{1a}$-immunized mammal with myeloma cells, said hybridoma HbMZ being capable of producing the antibody MZ.

In a further composition aspect of this invention, there is also provided a cell strain HZ-1 formed as a result of transformation of human lymphocytes by EB virus infection, said cell strain HZ-1 being capable of producing the antibody MZ.

In a still further composition aspect of this invention, there is also provided a reagent adapted to detect or quantify the ganglioside GDIa comprising a resin and the anti-ganglioside $GD_{1a}$ monoclonal antibody adsorbed on a surface of the resin.

In method aspects of this invention, this invention relates to a diagnostic method for diagnosing pathological conditions which elevate the level of the ganglioside $GD_{1a}$ in the blood, e.g., cancer, SLE and diseases resulting from an organic injury of the nervous system using the anti-ganglioside $GD_{1a}$ monoclonal antibody reagent of this invention and to methods of producing the $GD_{1a}$ monoclonal antibody of this invention.

The anti-$GD_{1a}$ monoclonal antibody according to this invention is extremely specific to $GD_{1a}$ and has a high antibody titer against $GD_{1a}$. As will become apparent from examples to be described subsequently, the monoclonal antibody does not react to other gangliosides having a saccharide chain similar to that of $GD_{1a}$ and reacts with extremely high specificity to $GD_{1a}$. Accordingly, $GD_{1a}$ can be quantified with extremely high sensitivity by using the anti-$GD_{1a}$ monoclonal antibody according to this invention. Since use of the monoclonal antibody according to this invention permits high-sensitivity quantification of $GD_{1a}$ in the blood, the probability that a tested subject may be suffering from a cancer or SLE or a disease resulting from an organic injury of the nervous system can be determined with good sensitivity by the reagent according to this invention which contains the monoclonal antibody of this invention. Furthermore, the hybridoma HbMZ and cell strain HZ-1 are novel and can produce the monoclonal antibody.

BRIEF DESCRIPTION OF THE DRAWING

The above and other objects, features and advantages of the present invention will become apparent from the following description and the appended claims, taken in conjunction with the accompanying drawing, which shows the concentrations of $GD_{1a}$ in the blood of various cancer patients and SLE patients as determined by an enzyme-linked immunosorbent assay (ELISA) making use of the monoclonal antibody $GD_{1a}$ antibody $MZ_{-1}$ according to this invention.

DETAILED DESCRIPTION OF THE INVENTION AND PREFERRED EMBODIMENTS

In the present application, the terms of glycolipids and lipids, the naming of binding types, etc., follow their corresponding general or common names in the present field of research. The structures of the glycolipids used are shown below in Table 3.

Anti-ganglioside $GD_{1a}$ Monoclonal Antibody MZ

The monoclonal antibody MZ according to this invention specifically binds $GD_{1a}$ and its specificity is extremely high. As will become apparent from the subsequent examples, the antibody titer of the monoclonal antibody MZ of this invention against $GD_{1a}$ is extremely high, e.g., at least $2^{16}$ and for all practical purposes does not exhibit any specific reaction to saccharide chains similar to that of $GD_{1a}$ or other glycolipids containing one of such saccharide chains, namely, GalCer, LacCer, $Gb_3$, $G_4$, $GA_2$, $GA_1$, $GM_3$, $GM_2$, $GM_1$, $GD_{1b}$, $GT_{1b}$, $GQ_{1b}$, Fuc-$GM_1$, $nLc_4$ and sialosyl $nLc_4$, in which Gal means galactose, Cer=Ceramide, Lac=lactose, Fuc =fucose and $nLc4$=paragloboside, and the antibody titers of the monoclonal antibody against such other glycolipids are not higher than $2^2$.

$GD_{1a}$ Immunization Method to Produce MZ-Containing Cells

The immunization method of this invention comprises the steps of:

(a) either injecting into a mammal or mixing with living cells capable of producing MZ an aqueous solution of the ganglioside $GD_{1a}$ or of a solution or suspension of a source of the $GD_{1a}$, in a physiologically acceptable aqueous fluid liquid and in an amount effective to stimulate the production of an isolable amount of the anti-ganglioside $GD_{1a}$ monoclonal antibody MZ; and (b) recovering the thus-produced MZ.

The antibody MZ according to this invention can be produced by each of the following two processes, namely, by a process in which a hybridoma is formed by fusion of antibody-producing cells of a mammal and myeloma cells (hereinafter called "hybridoma process") or by a process in which human B-lymphocytes are infected by EB virus (hereinafter called "EBV") to induce transformation (hereinafter called "EBV transformation process"). $GD_{1a}$ can be produced by screening an anti-$GD_{1a}$ antibody producing clone as a monoclone from antibody-producing cells imparted with proliferativeness in accordance with either one of the above processes and then selectively obtaining the monoclonal antibody having the abovedescribed characteristics.

Hybridoma HbMZ

The hybridoma HbMZ and process for its production will next be described in detail. In this invention, the formation of a hybridoma can be conducted in accordance with a known process, for example, the process described in Nature 256, 495 (1975), a modification thereof [Journal of Experimental Medicine, 150, 1008 (1979)] or the like.

Although no particular limitation is imposed on the species of animal and its organ to be employed for the production of $GD_{1a}$ for use as an immunogen, $GD_{1a}$ can most readily be isolated from an organ containing it in a large amount, for example, from the brain of an animal such as bovine. $GD_{1a}$ employed in the subsequent examples and tests were separated and purified from bovine brains in a manner known per se in the art unless otherwise specifically indicated. In addition to purified $GD_{1a}$, various cells having $GD_{1a}$ on their surfaces as well as substances or cells containing the saccharide chain, i.e., the antigen determinant of $GD_{1a}$, can also be used as immunogens.

Although no particular limitation is imposed on the species of animal to be immunized with $GD_{1a}$ it is however desirable to choose a mammal, in view of its compatibility with myeloma cells employed for the cell fusion. In general, human, mouse or rat or, in some instances, rabbit or the like mammal may be used.

Both in vivo and in vitro methods can be used for the immunization by $GD_{1a}$. In the case of in vivo immunization, $GD_{1a}$, which is substantially free from other gangliosides, at a suitable concentration in a physiologically acceptable carrier, e.g., physiological saline or a phosphate-buffered buffer solution (hereinafter called "PBS"), is administered systemically to an animal, e.g., by intravenous, subcutaneous or intraperitoneal injection or the like, preferably in multiple dosages of about 2 to about 20 ug each. More specifically, it is preferable, when purified $GD_{1a}$ is used, to dilute the starting $GD_{1a}$ (or source thereof) with PBS or the like to a suitable concentration and then to administer the resultant solution, along with a conventional carrier, such as *Salmonella minnesota* or bovine serum albumin (hereinafter called "BSA"), to an animal from several times to somewhat more than ten times, at intervals of 4–14 days between doses, in amounts effective to stimulate the production by the mammal of an isolable amount of MZ, e.g., a total dose of 10–300 ug or so per animal. The above procedure is also followed when membrane components or cells themselves are used. For example, it is preferable to give a total dose of 1–100 mg/animal when membrane components are used or a total dose of $10^6$–$10^9$ cells per animal when cells per se are used. In this case, a suitable immunoadjuvant, for example, Freund's complete adjuvant may be used as needed. In this in vivo immunization, antibody-producing cells may be any one of spleen cells, lymph node cells, intraperitoneal lymphocytes and peripheral blood lymphocytes. It is however most preferable to use spleen cells on the fourth day after their final immunization.

When immunization is conducted in an in vitro system, so-called in vitro sensitization may be used. This is intended to develop cells, which produce an antibody against $GD_{1a}$, by culturing in vitro lymphocytes selected suitably from spleen cells, lymph node cells, intraperitoneal lymphocytes and peripheral blood lymphocytes together with $GD_{1a}$ as an immunogen for about 1 week. When $GD_{1a}$ is a purified product, it is cultured together with lymphocytes by dissolving same in a cell culture medium or adsorbing same on a suitable carrier such as sheep erythrocytes, liposome or *Salmonella minnesota*. When $GD_{1a}$-containing cells *per se* or their membrane components are used as the immunogen, they are either dissolved or suspended in a culture medium and are then cultured together with lymphocytes. When the cells per se are used as the immunogen, it is desirable to culture them with lymphocytes subsequent to a treatment which renders them cytostatic, such as mitomycin treatment or exposure to radiation.

Any culture media employed routinely for the culture of lymphocytes, such as PRMI-1640, Dulbecco's MEM (hereinafter called "D-MEM"), may be used for the culture of lymphocytes. It is however desirable to incorporate fetal calf serum (hereinafter called "FCS") to a concentration of 5–20% in the culture medium upon application. The in vitro sensitization by $GD_{1a}$ can be achieved efficiently when 2-mercaptoethanol (hereinafter called "2-ME") and poke weed mitogen (hereinafter called "PWM") are added to final concentrations of $5 \times 10^{-5}$ M and 5–30 µg/ml respectively as needed.

Although the optimum cell concentration at the time of culture of lymphocytes varies depending on the equipment used for the culture, a concentration of about $10^6$–$10^7$ cells/ml is preferred in general.

Purified $GD_{1a}$, $GD_{1a}$-containing cells and their membrane components are preferably used as immunogens at final concentrations of 1–20 ug/ml, 1–100 mg/ml and 0.1–10 mg/ml, respectively.

The thus-produced antibody-producing cells, obtained by an in vivo or in vitro immunization such as described above, and myeloma cells are thereafter fused together.

As the myeloma cells, various cells already known in the art, for example, mouse NS-1, P3, P3-UI, X45, X63.6.5.3. or SP2, rat Y3 or Agl.2.3, or like cells may be used.

Production of Hybridoma HbMZ

HbMZ is produced by fusing antibody-producing cells derived from a $GD_{1a}$-immunized mammal and myeloma cells, said hybridoma HbMZ being capable of producing the antiganglioside $GD_{1a}$ monoclonal antibody MZ.

The cell fusion employed to produce HbMZ can be conducted following any conventional method. For example, it may be carried out by incubating the antibodyproducing cells and the myeloma cells in a physiologically acceptable culture medium, preferably one which contains a fusion promoter.

As the fusion promoter, a water-soluble or dispersible polyethylene glycol, e.g., having an average molecular weight of 1000–6000 or so (hereinafter called "PEG"), Sendai virus or the like may be used by way of example. It is also possible to add an adjuvant such as dimethyl sulfoxide in order to increase the efficiency of fusion.

The ratio of antibody-producing cells, e.g., lymphocytes, to myeloma cells which can be employed can be the same as that employed in general prior art methods. For example, about 1–10 times as many lymphocytes as myeloma cells typically are used.

As the culture medium employed for the above-described fusion, a variety of the usual culture media used for the culture of cells may each be used. It is generally preferable to omit serum such as FCS.

The fusion can be effected by mixing predetermined amounts of the above-described immunized (MZ-containing) cells and the myeloma cells thoroughly in a culture medium, centrifuging the resultant mixture and removing the supernatant, mixing the centrifuged cells with a PEG solution, preferably one which has been heated in advance to about 37° C, to the culture medium at a suitable final concentration, e.g., about 30–60 w/v%. Thereafter, a suitable culture medium is added, followed by centrifugation to remove the supernatant. This procedure is preferably repeated. The hybridomas which form include HbMZ.

Screening of the desired hybridoma is conducted by culturing the mixture of fused cells in a conventional hybridoma selective medium. The above-described myeloma cell strain (HbMZ) is a hypoxanthine guanidine phosphoribosyl transferase (HGPRT) deficient strain and cannot hence grow in HAT medium which contains hypoxanthine, aminopterin adn thymidine. It is therefore only necessary to select cells which grow in HAT medium. It is necessary to culture the mixture of fused cells in HAT medium for a period of time sufficient to kill cells other than the desired hybridoma HbMZ, generally, for several days to several weeks.

The thus-obtained HbMZ hybridoma cells are then subjected to a conventional cloning technique, for example, limiting dilution or the soft agar technique, whereby the monocloning of the intended antibody-producing cell strain is achieved.

The screening of the antibody-producing strain may be conducted by one or more of various techniques employed commonly for the detection of antibodies, for example, ELISA [Japanese Journal of Experimental Medicine,51, 309 (1981)], the plaque technique, agglutination, Ouchterlony's agar diffusion, radio-immunoassay (RIA).

The monoclonal anti-$GD_{1a}$ antibody-producing cell strain can be thus obtained by the hybridoma process as described above.

Monoclonal Anti-$GD_{1a}$ Antibody Production by EBV Transformation

The following is a description of the preparation of the monoclonal anti-$GD_{1a}$ antibody by EBV transformation. This process is based on the principle that when living B-lymphocytes, e.g., mammalian and preferably human lymphocytes, are infected by EBV, not only proliferation of EBV occurs but also production of antibodies is induced in each of the B-lymphocytes. EBV basically acts not only on B-lymphocytes of a particular clone which generates the anti-$GD_{1a}$ antibody, but also on B-lymphocytes of all clones to induce proliferation of EBV and production of other antibodies therein. In this process, the clone which produces the desired antibody is identified and selected, subsequent to the infection of the B-lymphocytes by EBV, and the desired monoclonal antibody can then be produced by propagating only the thus-chosen clone.

The transformation of human lymphocytes by the above process can be conducted in a manner known per se in the art, for example, in the manner described in Nature 267, 52 (1979).

No particular limitation is imposed on the organ to be employed for obtaining B-lymphocytes, so long as it is a lymphoid organ. However, in view of the special requirement that it is a human-derived source, lymphocytes of the peripheral blood of a healthy subject are As a virus source, a culture serum of continually EBV-producing cells, for example, B-95-8 cells—EBV-infected marmot leucocyte cell strain [Proceedings of the National Academy of Science of USA, 70, 190 (1973)] —may be used by way of example.

In this process, B-lymphocytes are first of all infected by EBV. Here, it is not necessary to separate B-lymphocytes alone from the lymphocyte fraction. It is only necessary to have lymphocytes, which have been obtained by a usual method, infected by EBV.

First of all, lymphocyte pellets are added with an EBV solution in an amount of about 10 ml per $10^7$ lymphocytes, followed by incubation for 1 hour at 37° C.

under 5% $CO_2$ so that the lymphocytes are infected by EBV.

The infected lymphocytes thus obtained are dispersed in a cell culture medium, followed by incubation for 2-5 weeks at 37° C. under 5% $CO_2$.

No particular limitation is imposed on the culture medium. Any culture medium may be used, so long as it is generally employed for the culture of lymphocytes, such as RMPI-1640 or D-MEM. It is preferable to add FCS at a concentration of 10-20% to the culture medium upon application. Addition of glutamine to the medium at a final concentration of 0.5-1 mg/ml allows the cells to proliferate more efficiently.

The transformed B-lymphocytes obtained in the above manner are then processed in the same manner as in the above-described hybridoma process so as to conduct the screening and monocloning of the intended antibody-producing strain.

As in the hybridoma process, the screening of the antibody-producing strain can be carried out by one or more of various techniques employed generally for the detection of antibodies, such as ELISA, RIA and the like.

The MZ-producing cell strain can also be obtained by EBV transformation as described above.

The above-described MZ-producing cell strain can be subcultured in an ordinary medium and can be stored readily for a long period of time in liquid nitrogen, whether its preparation process is the hybridoma process or the EBV hybridoma process.

The present inventors have already deposited, as one example of MZ-producing strains, the hybridoma HbMZ-1 obtained in the below-described Example, under the name of "MZ-1" with Institute for Fermentation Osaka, 17-85, Juso-honmachi 2-chome, Yodogawa-ku, Osaka 532, Japan (Accession Number: FERM-BP-2058).

Anti-ganglioside $GD_{1a}$ Monoclonal Antibody MZ Reagent

In order to obtain the MZ of this invention from the specific cell strain obtained in a manner as described above, it is necessary to culture the cell strain on a large scale by a method known per se in the art and then to separate MZ from the culture supernatant or to administer the cell strain to a mammal compatible with the cell strain, to allow it to proliferate and then separate MZ from the serum or ascitic fluid.

Since MZ of this invention can specifically recognize $GD_{1a}$ alone with extremely high sensitivity, it has utility as a reagent for the high-sensitivity detection or quantification of $GD_{1a}$. As already mentioned above, it has been reported that the composition of gangliosides in the blood of a cancer or SLE patient is different significantly from that of healthy people [Journal of Biochemistry, 98, 843 (1985)]. Accordingly, MZ of this invention also has utility as a diagnostic reagent for cancers, especially solid and methasized internal cancers, e.g., tumors or organs such as stomach, liver, pancreas, lung, breast, colon, prostate, etc., and for SLE and to diagnose pathological conditions resulting from an organic injury to the nervous system.

Immunological identification and quantification of $GD_{1a}$ by a reagent of this invention, which contains MZ, can be conducted in a manner similar to the immunological quantification of general biosubstances. Although no particular limitation is imposed on the manner employed, radioimmunoassay (RIA), ELISA, thin layer chromatography (hereinafter called "TLC"), immunostaining, immunohistochemistry or the like may be used. The socalled competition technique, sandwich technique or the like may be used in RIA and ELISA, although not necessarily limited thereto.

Needless to say, the immunological identification and quantification of $GD_{1a}$ by the reagent of this invention are not necessarily applied only to $GD_{1a}$ in the blood of a cancer patient, SLE patient or patient having an organic injury in the nervous system but may also be applied widely to $GD_{1a}$ in bloods, body fluids, organs or excreta of men and various experimental animals.

The MZ's usefulness as a diagnostic reagent is enhanced by immobilizing it, e.g., at a concentration of from about 5 to about 100 nm/mg, on an insoluble resin which absorbs antibodies. Many of these are known in the prior art, e.g., polystyrene, (list others, generically and specifically).

As will be demonstrated in Test 3 described below, the epitope recognized by MZ of this invention is its own saccharide chain structure of $GD_{1a}$ like those of monoclonal antibodies against other glycolipids. The reagent of this invention is therefore useful for the detection and quantification of not only $GD_{1a}$ but also of molecules having the saccharide chain structure of $GD_{1a}$.

Use of MZ as a Diagnostic Reagent

As will become apparent in Test 4 described below, the concentrations of $GD_{1a}$ in body fluids of cancer patients and SLE patients increase. The changes are however small, viz., from several times to somewhat greater than 10 times their corresponding normal levels. It is not possible to detect changes of such a small magnitude with good sensitivity so long as conventional polyclonal antibodies are used. When a conventional chemical analysis is relied upon, ganglioside is required in a large quantity. As described in Journal of Biochemistry, 98, 843 (1985), whose disclosure is incorporated herein by reference, the blood of a patient is passed through a column of immobilized protein A via an external circuit, so that immunoglobulin G is adsorbed, in the form of an immune complex with ganglioside, in the column and the complex is then recovered from the column to obtain ganglioside. It is however practically impossible for a patient reduced in both strength and activity such as a cancer patient to be subjected to the stress of such a diagnostic procedure.

In one aspect, the reagent of this invention is in the form of an adsorbent resin having adsorbed on a surface thereof an amount of the anti-ganglioside $GD_{1a}$ monoclonal antibody MZ effective to render the resin $GD_{1a}$-reactive. An example of a suitable resin is polystyrene. Any other non-reactive, preferably particulate resin which adsorbs proteins on an exterior surface thereof, e.g., those used to immobilize enzymes, can be used. The amount of MZ adsorbed thereon typically is 5 to 100 nm per mg of resin, preferably about 25 to 75 nm per mg.

Because the reagent of this invention has extremely high sensitivity, the quantification of $GD_{1a}$ is feasible by sampling a small amount of blood from a patient. The present invention has therefore made it possible for the first time to perform practical diagnoses of cancers and SLE, e.g., employing the same techniques as described in the above-cited J. Biochem. article.

Accordingly, in a method-of-use aspect of this invention, this invention relates to a method wherein the lymphocytes are human lymphocytes.

The present invention will hereinafter be described more specifically by the following Examples and Tests.

EXAMPLE 1

Purified $GD_{1a}$ (100 ug) and formalin-treated Salmonella minnesota (ATCC 9700) (400 ug) were added to 4 ml of a physiological saline maintained warm at 40° C., followed by thorough stirring into a uniform suspension. The resultant suspension was intravenously administered at a dose of 10 ug in terms of $GD_{1a}$ per administration to each of a mouse and a rat every 4th day 4-15 times in total. Their spleens were then removed on the 4th day after the final administration, followed by cell fusion of $3 \times 10^8$ spleen cells and $3 \times 10^7$ NS-1 mouse myeloma cells (ATCC TIB18) in the presence of 50% polyethylene glycol. The resultant hybridomas were poured in aliquot portions into the wells of a plastic culture plate with 96 flat-bottomed wells ("FALCON", trademark) and were then cultured at 37° C. under 5% $CO_2$ in D-MEM medium containing HAT medium and added with 10% of FCS. With respect to each well in which growth of hybridomas was observed, the presence or absence of the anti-$GD_{1a}$ antibody in the culture supernatant was tested by an enzyme-linked immunosorbent assay (ELISA) to be described next. ELISA was conducted in the following manner: Using a 96-well plastic plate ("FALCON", trademark), a 10 ug/ml solution of $GD_{1a}$ in ethyl alcohol was poured in 0.05 ml portions into the individual wells. The solvent was allowed to evaporate naturally, so that $GD_{1a}$ was adsorbed on the plate. Each well was filled with a test culture supernatant as a primary antibody so as to permit a thorough reaction. After washing the well thoroughly, an anti-mouse immunoglobulin antibody (where the mouse was used as an immune animal) or anti-rat immunoglobulin antibody (where the rat was used as an immune animal) labelled with peroxidase was caused to react as a secondary antibody.

A peroxidase reaction making use of diammonium 2,2'-azinobis(3-ethylbenzthiazolinesulfonate) as a substrate was then conducted. The degree of staining in each well was then determined either visually or by using an automatic photometer for 96-well ELISA (wavelength: 414 nm). The hybridomas in each well where a substantial anti-$GD_{1a}$ antibody titer was observed in the culture supernatant were subjected to cloning by limiting dilution, so that monocloning was achieved.

The thus-obtained monoclonal hybridoma was cultured in a large quantity in a plastic culture flask, thereby obtaining the desired monoclonal anti-$GD_{1a}$ antibodyproducing cell strain. The cell strain was transplanted to a nude mouse treated in advance with pristane (2,6,10,14-tetramethylpentadecane, product of Aldrich Company) as an immunosuppressant. An antibody was obtained in a purified form from the resulting ascitic fluid by the 50% saturated ammonium sulfate method.

It was possible to obtain the monoclonal anti-$GD_{1a}$ antibody as described above. The antibody was named as "MZ". The MZs used as antibodies in the subsequent tests were "MZ-1", mouse-derived monoclonal anti-$GD_{1a}$ antibody, and "MZ-2", rat-derived monoclonal anti-$GD_{1a}$ antibody. Further, the hybridoma capable of producing such MZ antibodies was named "HbMZ". The hybridomas obtained by using mouse cells and rat cells separately in this Example were numbered "HbMZ-1" and "HbMZ-2", respectively.

EXAMPLE 2

After preparing lymphocytes (mononuclear cells) from human peripheral blood in a usual manner by using Ficoll Paque (tradename; product of Pharmacia AB), they weresuspended at a concentration of $1 \times 10^7$ lymphocytes/ml in a culture medium.

RMPI-1640 medium added with 10% FCS was used as the culture medium. At the time of use, 2-ME and PWM were added to final concentrations of $5 \times 10^{-5}$ M and 30 ug/ml respectively. Thereafter, 1 ml of the lymphocyte suspension of the concentration of $1 \times 10^7$ lymphocytes/ml was placed in the inner cylinder of a Marbrook culture bottle [Lancet, 2, 1279 (1967)], while 10 ml of a PWM-free culture medium was placed in its outer cylinder. A dialysis tube was placed at the boundary between the inner cylinder solution and the outer cylinder solution.

$GD_{1a}$ was incorporated in a liposome prepared in accordance with the method of Uchida et al. [Journal of Biochemistry, 87, 1829 (1980)]and formed of yolk lecithin and cholesterol, and was then added to a final $GD_{1a}$ concentration of 5 ug/ml into the inner cylinder of the culture bottle.

The lymphocytes were thereafter cultured together with $GD_{1a}$ at 37° C. under 5% $CO_2$ for 6 days. Cell fusion with mouse myeloma cells NS-1 and cloning of MZ-producing hybridoma were then conducted in a similar manner as in Example 1, thereby obtaining one clone of MZ-producing strain. It was numbered as "HbHZ-1".

In this example, peroxidase-labelled anti-human immunoglobulin antibody was used as the secondary antibody in the ELISA.

EXAMPLE 3

First of all, B-95-8 cells (ATCC CRL1612) which were continually producing and releasing EBV were suspended at a concentration of $3 \times 10^5$ cells/ml in RPMI-1640 medium containing glutamine at a final concentration of 0.86 mg/ml and added with 20% FCS. The cells were cultured at 37° C. under 5% $CO_2$. The culture supernatant obtained 7 days later was provided as a virus solution employed hereinbelow.

Based on usual procedures, pellets of lymphocytes obtained by using Ficoll Paque (trademark) were then added and mixed with the virus solution in a proportion of 10 ml per $1 \times 10^7$ lymphocytes, followed by incubation at 37° C. under 5% $CO_2$ for 1 hour. The EBV-infected lymphocytes were suspended at a concentration of $2 \times 10^5$ to $6 \times 10^5$ lymphocytes/ml in a complete culture medium. The suspension was poured in 0.1 ml portions into the individual wells of a plastic culture well with 96 flat-bottomed wells ("FALCON", trademark). Their culture was started at 37° C. under 5% $CO_2$. Four days later, each well was added with 0.1 ml of a fresh supply of the complete culture medium. The culture was thereafter continued while replacing one-half of the culture supernatant in each well with a fresh supply of the complete culture medium at intervals of 3-4 days. Two-four weeks later, the anti-$GD_{1a}$ antibody titer in the culture supernatant in each well where proliferation of cells was observed was measured by the ELISA described in Example 1. Incidentally, peroxidase-labelled anti-human immunoglobulin was used as a secondary antibody.

Using a 24-well culture plate, a 6-well culture plate and a 6-cm plastic dish successively, cells in each well in which a high anti-$GD_{1a}$ antibody titer was observed in the supernatant were cloned by the soft agar technique in a usual manner, so that a single clone of monoclonal anti-$GD_{1a}$ producing cell strain was obtained. It was named as cell strain "HZ-1".

From a culture supernatant obtained by culturing the culture strain in a large amount, MZ according to this invention was obtained by the 50%-saturation ammonium sulfate precipitation method. It was numbered as "MZ-3".

Test 1

The classes of the immunoglobulin antibodies MZ-1 and MZ-2 obtained in Example 1 were determined by ELISA. Namely, each of antibodies against peroxidase-labelled mouse immunoglobulins of the individual classes was reacted to each MZ, followed by a peroxidase reaction while using ABTS as a substrate.

As a result, MZ-1 and MZ-2 were both found to belong to the class of IgM.

Test 2

The reactivity of each of the MZs obtained in Examples 1 and 3 to various glycolipids was investigated by ELISA. The glycolipids included, in addition to $GD_{1a}$, CalCer (bovine-brain-derived), LacCer (bovine-brain-derived), $Gb_3$ (human-erythrocyte-derived), $Gb_4$ (human-erythrocyte-derived), $GA_2$ (bovine-brain-derived), $GA_1$ (bovine-brain-derived), $GM_3$ (bovine-brain-derived), $GM_2$ (bovine-brain-derived), $GM_1$ (bovine-brain-derived), $GD_{1b}$ (bovine-brain-derived), $GT_{1b}$ (bovine-brain-derived), $GQ_{1b}$ (bovine-brain-derived), Fuc-$GM_1$ (raterythrocyte-derived), $nLc_4$ (human-erythrocyte-derived) and sialosyl $nLc_4$ (bovine-erythrocyte-derived), all of which has a structure analogous to the structure of $GD_{1a}$ as shown subsequently in Table 3. The antibody titer against each of the glycolipids is indicated by its maximum doubling dilution (expressed in terms of involution of 2) at which staining was still recognized visually by ELISA.

As a result, each MZ showed a high antibody titer against $GD_{1a}$. Namely, the MZ obtained in Example 1 had an antibody titer of $2^{18}$ against $GD_{1a}$. It was $2^{16}$ in the case of the MZ of Example 3. However, neither the former MZ nor the latter MZ reacted to the other glycolipids (their antibody titers were all not greater than $2^2$).

Test 3

The glycolipid specificity of each of the MZs obtained in the above Examples was studied further by a TLC-immunostaining technique. According to this technique, glycolipids are fractionated by TLC on silica gel and immunostaining is conducted on a thin-layer plate thereof by using the same principle as ELISA. This technique has the advantages that its sensitivity in the detection of each glycolipid is very high and reactions to substances mixed at trace levels in each glycolipid can be prevented. Accordingly, it is now used widely in the present field of research as one of the best techniques for the investigation of the specificity of an antibody to a glycolipid.

In this Test, TLC-enzyme immunostaining was conducted following the technique reported by Azuma et al. [Journal of Biochemistry, 95, 1517 (1934)].

First of all, various glycolipids led by $GD_{1a}$, whose origins are as described in Test 2), were spotted on a thin-layer plate of silica gel ("POLYGRAM SIL G", tradename; product of Macherey-Nagel Company).

They were developed for about 25 minutes by using a 50:40:10 (v/v) mixture of chloroform, methyl alcohol and a 0.25% solution of potassium chloride as a solvent. The positions of the individual glycolipids after the development were determined with orcinol.

Concurrently with the development for the orcinol reaction, development was also conducted for immunostaining. Staining was conducted in the following manner. First of all, one of the MZs prepared in Examples 1 and 3 and polyclonal anti-$GD_{1a}$ rabbit antibody was reacted as a primary antibody to the thus-developed thin-layer plate. Used with the polyclonal anti-$GD_{1a}$ rabbit antibody was an antiserum obtained by immunizing a rabbit with $GD_{1a}$ and then collecting the blood two weeks after a booster. An antibody (labelled with peroxidase) against mouse, human or rabbit immunoglobulin was suitably chosen and was reacted as a secondary anti-body to the plate. Using 4-chloro-1-naphthol as a substrate, staining was then conducted by a peroxidase reaction.

As a result, each MZ of this invention reacted only to the spot of $GH_{1a}$ as shown in Table 1. The polyclonal anti-$GD_{1a}$ antibodies used as controls reacted not only to $GD_{1a}$ but also to $GM_1$ and $GD_{1b}$.

TABLE 1

| | Enzyme immunostaining[1] | | | |
|---|---|---|---|---|
| Glycolipid | MZ-1 | MZ-2 | MZ-3 | Rabbit antibody |
| GalCer | − | − | − | − |
| LacCer | − | − | − | − |
| $Gb_3$ | − | − | − | − |
| $Gb_4$ | − | − | − | − |
| $nLc_4$ | − | − | − | − |
| Sialosyl $nLc_4$ | − | − | − | − |
| $GM_3$ | − | − | − | − |
| $GM_2$ | − | − | − | − |
| $GA_2$ | − | − | − | − |
| $GM_1$ | − | − | − | + |
| $GA_1$ | − | − | − | − |
| $GD_{1a}$ | + | + | + | + |
| $GD_{1b}$ | − | − | − | + |
| $GT_{1b}$ | − | − | − | − |
| $GQ_{1b}$ | − | − | − | − |
| Fuc-$GM_1$ | − | − | − | − |

[1]Sign (−) indicates no staining while sign (+) shows existence of staining.

From the above results, MZ obtained in Example 1 and MZ obtained in Example 3 have both demonstrated specificity to $GD_{1a}$ alone. Due to this specificity, these monoclonal anti-$GD_{1a}$ antibodies show high superiority to the polyclonal anti-$GD_{1a}$ rabbit antibody which has been prepared by known methods and has been used to date.

Further, it may be concluded from the results of this Test that the monoclonal anti-$GD_{1a}$ antibody according to this invention recognizes the saccharide chain structure of SAα2—3Galβ1—3GalNAcβ1—4[SAα2—3]-Galβ1→4Glc.

Test 4

Polystyrene beads with protein A immobilized thereon were placed in a glass test tube and 1 ml of the serum of a cancer or SLE patient was poured further into the test tube. The test tube was stored at 4° C. overnight. The polystyrene beads were washed. With a 0.3 M glycine-HCl buffer (pH 2.8), the immune complex was then released from protein A and the immune complex itself was caused to dissociate further into $GD_{1a}$ and immunoglobulin G. The polystyrene beads were taken out of the test tube. The test tube was added with 12 ml of a 2:1 (v/v) mixture of chloroform and methyl alcohol and was then shaken well. After centrifugation, the fraction of the lower chloroform layer was collected and was then evaporated to dryness. It was then dissolved in a suitable amount of PBS containing 1% of BSA, thereby providing a sample for the following $GD_{1a}$ measurement.

The measurement of $GD_{1a}$ was conducted by using the following enzyme-linked immunosorbent assay. Firstly, 100 ul portions of the sample were placed respectively in the individual wells of a 96-well microtitration plate (hereinafter called "plate"). Polystyrene beads with MZ of this invention conjugated therewith were then added. The plate was incubated at 37° C. for 3:hours. After washing the plate, each well was added with 100 ul of biotinylated MZ (the biotinylation was conducted by a method known per se in the art, see *Cell Biology*, 73783 (1977), which was dissolved in PBS containing 1% of BSA and 0.05% of Tween 20 (tradename., polyoxyethylene-sorbitan monolaurate), followed by a reaction at room temperature for 1 hour. After washing the plate, to each well was added peroxidase-labelled avidin dissolved in PBS which contained 1% of BSA and 0.05% of Tween 20. The plate was then maintained at room temperature for 1 hour. After washing, a peroxidase reaction was conducted, using ABTS as a substrate. The degree of staining of each well was then measured by means of an automatic photometer for 96-well ELISA. $GD_{1a}$ was sealed in liposome by the method described in Example 2. Based on a standard curve making use of the liposome, $GD_{1a}$ concentrations were determined.

The results established that cancer patients and SLE patients have higher $GD_{1a}$ values compared with healthy subjects, as shown in the drawing. Further, high $GD_{1a}$ values were observed, irrespective of the type of cancer. Since $GD_{1a}$ concentrations plotted along the axis or ordinates are shown by converting them in accordance with a specific concentration unit (U/ml), the drawing shows relative relationship among the samples.

As has been described above, the monoclonal antiGD$_{1a}$ antibody according to this invention and the blood $GD_{1a}$ level assay system making use of the antibody are extremely useful for the diagnoses of cancers and SLE.

Test 5

In this test, the blood level of $GD_{1a}$ in the course of development of experimental allergic encephalo-myelitis as an animal model of multiple sclerosis, which is a human disease accompanied by an organic injury such as brain demyelination, was assayed by using the monoclonal anti-GD$_{1a}$ antibody obtained in Example 1.

First of all, an emulsion of the spinal cord of a guinea pig and Freund's complete adjuvant (hereinafter called "FCA") was administered to a group of five female Lewis rats having a body weight of about 180 g at the soles of their hind paws. Blood was collected from each rat 1-4 weeks later to measure the concentration of $GD_{1a}$ in the blood. The quantification of $GD_{1a}$ was conducted in accordance with ELISA in which the monoclonal anti-GD$_{1a}$ antibody MZ-2 obtained in Example 1 was used (details are described in Test 4 above).

Results are summarized in Table 2. Since each $GD_{1a}$ concentration in the table is an average of values of five rats converted in accordance with a given concentration unit (U/ml), the values indicate relative values of test groups. In the animal model of the present test, it is known that the phenomenon of demyelination takes place in the brain of a rat from about 3 weeks after the challenge with the above-described emulsion of the spinal cord of a guinea pig and FCA. As shown in Table 2, the blood level of $GD_{1a}$ increases from the third week after administration in the group administered with the spinal cord of a guinea pig and FCA.

As is envisaged from the foregoing, the monoclonal antibody according to this invention has been indicated to be useful for the diagnoses of various diseases accompanied by an organic injury of the nervous system.

TABLE 2

| Administered for challenge | Blood level of $GD_{a1}$ (U/ml) | | | |
|---|---|---|---|---|
| | 1 week later | 2 weeks later | 3 weeks later | 4 weeks later |
| FCA alone | <5 | <5 | <5 | <5 |
| Spinal Cord + FIA[1] | <5 | <5 | <5 | |
| Spinal Cord + FCA | <5 | <5 | 178 | 106 |

[1]Freund's incomplete adjuvant free of *tubercule bacilli*.

In Tests 4 and 5, the monoclonal antibody of this invention was used as the "insolubilized" antibody conjugated on the polystyrene beads and the biotin-labelled antibody respectively. A linear standard line was obtained in an extremely low $GD_{1a}$ concentration range of 1-10 ng/ml.

When the insolubilized antibody and labelled antibody were both the polyclonal anti-GD$_{1a}$ rabbit antibody which had been used conventionally, a linear standard line was obtained in a concentration range of 10-100 ng/ml.

On the other hand, a straight standard line was obtained in a concentration range of 5-50 ng/ml when the monoclonal antibody $GD_{1a}$ and the polyclonal anti-GD$_{1a}$ rabbit antibody were used as an insolubilized antibody and a labelled antibody respectively.

In the $GD_{1a}$ assay employed in Tests 4 and 5, in other words, by the so-called sandwich technique, the sensitivity of the assay increased by the use of the monoclonal antibody.

In the quantification of $GD_{1a}$ by the so-called competition technique, a straight standard line was also obtained at $GD_{1a}$ concentrations in a range of 10-100 ng/ml when the polyclonal anti-GD$_{1a}$ antibody was used. A straight standard line was however obtained in a range of 3-30 ng/ml when MZ of this invention was used.

As has been described above, assay systems of higher assay sensitivity compared with those available from the use of a polyclonal antibody were obtained when the monoclonal antibody of this invention was used for the assay of $GD_{1a}$. It has hence become feasible to detect variations in the concentration of $GD_{1a}$ in a body fluid in a diseased state, although it was conventionally impossible to assay such variations by any assay system making use of a polyclonal antibody. This is a further advantage of MZ, the monoclonal anti-GD$_{1a}$ antibody of this invention, over the conventional polyclonal anti-GD$_{1a}$ antibodies.

TABLE 3

| Glycolipid | Structure |
| --- | --- |
| GalCer | Gal$\beta$1 → 1Cer |
| LacCer | Gal$\beta$1 → 4Glc$\beta$1 → 1Cer |
| Gb$_3$ | Gal$\alpha$1 → 4Gal$\beta$1 → 4Glc$\beta$1 → 1Cer |
| Gb$_4$ | GalNAc$\beta$1 → 3Gal$\alpha$1 → 4Gal$\beta$1 → 4Glc$\beta$1 → 1Cer |
| nLc$_4$ | Gal$\beta$1 → 4GlcNAc$\beta$1 → 3Gal$\beta$1 → 4Glc$\beta$1 → 1Cer |
| Sialosyl nLc$_4$ | SA$\alpha$2 → 3Gal$\beta$1 → 4Glc$\beta$1 → 3$\beta$Gal$\beta$1 → 4Glc$\beta$1 → 1Cer |
| GM$_3$ | SA$\alpha$2 → 3Gal$\beta$1 → 4Glc$\beta$1 → 1Cer |
| GM$_2$ | GalNAc$\beta$1 → 4[SA$\alpha$2 → 3]Gal$\beta$1 → 4Glc$\beta$1 → 1Cer |
| GA$_2$ | GalNAc$\beta$1 → 4Gal$\beta$1 → 4Glc$\beta$1 → 1Cer |
| GM$_1$ | Gal$\beta$1 → 3GalNAc$\beta$1 → 4[SA$\alpha$2 → 3]Gal$\beta$1 → 4Glc$\beta$1 → 1Cer |
| GA$_1$ | Gal$\beta$1 → 3GalNAc$\beta$1 → 4Gal$\beta$1 → 4Glc$\beta$1 → 1Cer |
| GD$_{1a}$ | SA$\alpha$2 → 3Gal$\beta$1 → 3GalNAc$\beta$1 → 4[SA$\alpha$2 → 3]Gal$\beta$1 → 4Glc$\beta$1 → 1Cer |
| GD$_{1b}$ | Gal$\beta$1 → 3GalNAc$\beta$1 → 4[SA$\alpha$2 → 8SA$\alpha$2 → 3]Gal$\beta$1 → 4Glc$\beta$1 → 1Cer |
| GT$_{1b}$ | SA$\alpha$2 → 3Gal$\beta$1 → 3GalNAc$\beta$1 → 4[SA$\alpha$2 → 8SA$\alpha$2 → 3]Gal$\beta$1 → 4Glc$\beta$1 → 1Cer |
| GQ$_{1b}$ | SA$\alpha$2 → 8SA$\alpha$2 → 3Gal$\beta$1 → 3GalNAc$\beta$1 → 4[SA$\alpha$2 → 8SA$\alpha$2 → 3]Gal$\beta$1 → 4Glc$\beta$1 → 1Cer |
| Fuc-GM$_1$ | Fuc$\alpha$1 → 2Gal$\beta$1 → 3GalNAc$\beta$1 → 4[SA$\alpha$2 → 3]Gal$\beta$1 → 4Glc$\beta$1 → 1Cer |

In the Table, Glc: glucose, Gal: galactose, GlcNAc: N-acetylglucosamine, GalNAc: N-acetylgalactosamine, SA: sialic acid, and Cer: ceramide.

What is claimed is:

1. An antiganglioside GD$_{1a}$ monoclonal antibody capable of recognizing the glycolipid GD$_{1a}$, and essentially incapable of specifically binding the glycolipids GalCer, LacCer, Gb$_3$, Gb$_4$, GA$_1$, GA$_2$, GM$_1$, GM$_2$, GM$_3$, GD$_{1b}$, GT$_{1b}$, GQ$_{1b}$, Fuc-GM$_1$, nLc$_4$.

2. An antibody as claimed in claim 1, free from antibodies which are essentially capable of specifically binding a glycolipid other than GD$_{1a}$.

3. An antibody as claimed in claim 1, wherein the antibody titer thereof against GD$_{1a}$ is at least $2^{16}$.

4. A screening reagent for cancers of systemic lupus erythematosus (SLE), comprising a reagent adapted to detect or quantify GD$_{1a}$, comprising an antibody as claimed in claim 1 and a diagnostically acceptable carrier therefor.

5. A method of screening for cancer, systemic lupus erythematosus (SLE) and pathological conditions of the nervous system resulting from an organic injury, which comprises the steps of:

(a) binding ganglioside GD$_{1a}$ present in a mixture of gangliosides in the serum of a sample of mammalian blood from an individual being diagnosed for cancer, SLE or a pathological condition of the nervous systems to an anti-ganglioside GD$_{1a}$ monoclonal antibody;

(b) separating the thus-produced GD$_{1a}$-antibody complex from the other gangliosides; and (c) detecting and determining the relative proportion of GD$_{1a}$ present in the sample of blood compared to that present in a corresponding sample of blood from a healthy human being.

6. A method of claim 4, wherein the method of detecting and determining the GD$_{1a}$ is enzyme-linked immunosorbent assay or radioimmunoassay.

7. A diagnostic reagent of claim 4, wherein the reagent further comprises a resin onto which the antibody is absorbed.

8. An antibody of claim 1, which is MZ-1 (FERM BP-2058).

9. A screening reagent of claim 4, wherein the antibody is MZ-1 (FERM BP-2058).

10. A method of claim 5, wherein the anti-ganglioside GD$_{1a}$ monoclonal antibody is MZ-1 (FERM BP-2058).

* * * * *